United States Patent [19]
Scheeren et al.

[11] Patent Number: 5,183,913
[45] Date of Patent: Feb. 2, 1993

[54] CYCLIC TRIKETONE COMPOUNDS AND TRIMETHYLSILYOXY BUTADIENE COMPOUNDS AND THEIR USE IN THE PREPARATION OF DAUNOMYCINONE DERIVATIVES

[75] Inventors: Johan W. Scheeren, Malden; Joannes F. Martinus De Bie, Nijmegen; Dirk De Vos, Oegstgeest, all of Netherlands

[73] Assignee: Pharmachemie B.V., Haarlem, Netherlands

[21] Appl. No.: 812,902

[22] Filed: Dec. 20, 1991

Related U.S. Application Data

[62] Division of Ser. No. 473,538, Feb. 1, 1990, Pat. No. 5,097,051.

[30] Foreign Application Priority Data

Feb. 10, 1989 [NL] Netherlands .......................... 8900329

[51] Int. Cl.$^5$ .......................... C07F 7/08; C07F 7/10; C07F 7/18
[52] U.S. Cl. .......................... 556/446; 556/423; 556/427; 556/448
[58] Field of Search ................. 556/423, 446, 427, 448

[56] References Cited

U.S. PATENT DOCUMENTS 4,772,683 9/1988 Martel et al. .................. 556/423 X
5,061,817 10/1991 Ohashi et al. .................. 556/446 X Primary Examiner—Paul F. Shaver
Attorney, Agent, or Firm—Browdy and Neimark

[57] ABSTRACT

The invention provides novel cyclic triketone compounds of the formulae

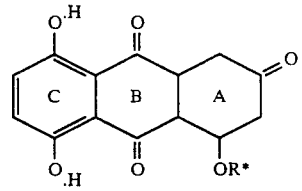

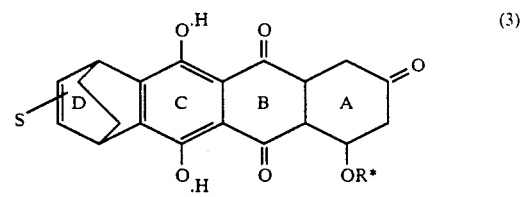

wherein S is H, alkyl or alkoxy and R* is a group of the formule

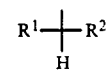

wherein $R^1$ is methyl and $R_2$ is an alkyl group containing at least 2 carbon atoms or $R^1$ is an alkyl group having 1–4 carbon atoms and $R^2$ is an aryl group, a hetero aryl group, a —$CH_2OR'$ group, a —$CH_2N<$ group, a —$CH_2SR''$ group or a —$CH_2CH=CH_2$ group, wherein R' and R'' are alkyl groups having 1–4 carbon atoms.

These compounds can be used for preparing daunomycinone and derivatives thereof. Daunomycinone is used for preparing daunomycin and adriamycin. By introducing chirality at C-1 of ring A in the preparation of said novel compounds by using a novel diene of formula (1) in a Diels-Alder reaction for said preparation, the chirality of C-3 is established in the subsequent reaction with $LiC\equiv CSi(CH_3)_3$ in the synthesis of daunomycinone and deriviatives thereof.

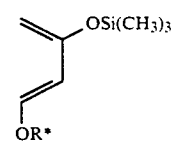

This last reaction leads to the desired compound wherein OH at C-3 and OR at C-1 are in the cis-position with respect to each other.

10 Claims, No Drawings

CYCLIC TRIKETONE COMPOUNDS AND TRIMETHYLSILYOXY BUTADIENE COMPOUNDS AND THEIR USE IN THE PREPARATION OF DAUNOMYCINONE DERIVATIVES

This is a division of application Ser. No. 07/473,538 filed Feb. 1, 1990, now U.S. Pat. No. 5,097,051.

This invention relates to cyclic triketone compounds and trimethylsilyloxy-1,3-butadiene compounds and their use in the preparation of daunomycinone derivatives.

Daunomycinone is a compound of the formula

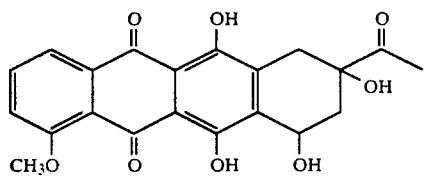

Derivatives thereof are daunomycin or daunorubicin (which has an antibiotic and antineoplastic activity) and adriamycin or doxorubicin (which also has an antibiotic and antineoplastic activity).

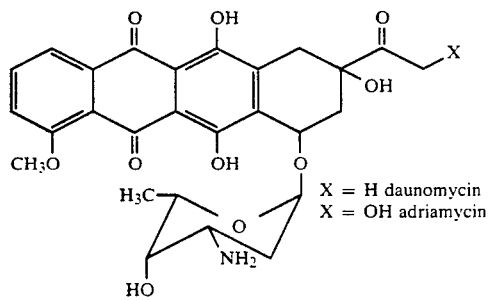

X = H daunomycin
X = OH adriamycin

The applicant employs the following reactions in the total synthesis of daunomycinone and derivatives thereof by analogy with the syntheses of T. R. Kelly et al, Tetrahedron, Vol. 40, no. 22, 4569–4577 (1984) and of K. Krohn and K. Tolkiehn, Chem. Ber. 112, 3453–3471 (1979).

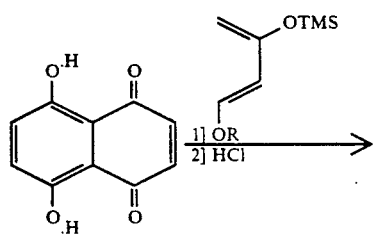

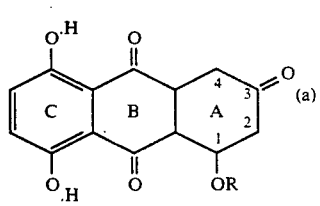

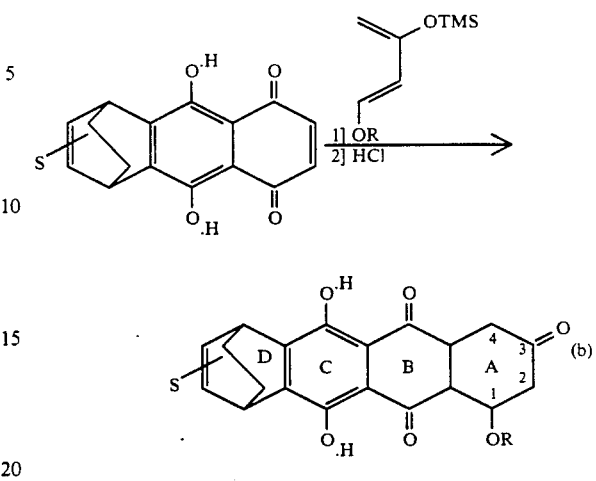

By using a group R* having an asymmetric C atom, chirality can be introduced at C-1 of ring A, and the chirality of C-3 is established in the subsequent reaction with LiC≡CSiMe₃, as the —C≡CSiMe₃ group is introduced exclusively cis to the C-1-OR group. vide schemes 1 and 2. The introduction of chirality at C-1 can be studied both with a racemic mixture of butadienes and by using only one enantiomer. The obtained cycloadducts have two asymmetric carbon atoms and therefore are obtained as mixtures of diastereomers. When using one enantiomeric diene, two diastereomers are produced, e.g. in the case of the R-diene the RR and RS stereoisomers in a ratio which is *not* equal to 1:1 (diastereomeric excess). When using a racemic mixture of the dienes, a mixture of the stereoisomers SS, RR, SR and RS is produced, in which mixture the amount of SR+RS differs from the amount of RR+SS, i.e. again a diastereomeric excess is present.

The diene should meet 3 requirements:
1) the diene should be reactive
2) The group —OR should be capable of being easily converted to an OH group
3) The reaction should proceed stereoselectively.

Examples of Diels-Alder reactions with a chiral diene, wherein an asymmetric carbon atom is introduced, are known in literature. By reacting 1-substituted-1,3-butadiene with juglone, Trost et al, J. Am. Chem. Soc., 102, 7595–7596 (1980) obtained a diastereomeric excess of 100% of the product:

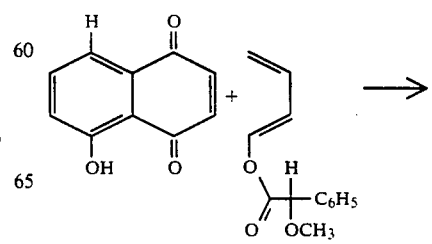

-continued

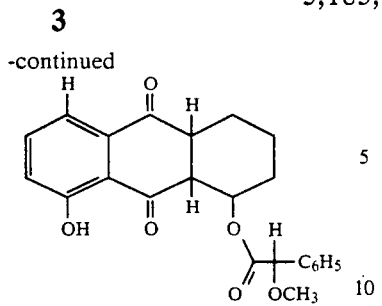

Because of the lack of a 3-functionality the diene employed is not useful for the above present reactions of diene and dienophilic quinone compounds.

R. C. Gupta et al, J. Chem. Soc. Perking Trans. I, 1773-1785 (1988) did achieve an asymmetric induction with a Diels-Alder reaction using 1,3-disubstituted 1,3-butadiene. The synthesis carried out by Gupta et al is as follows:

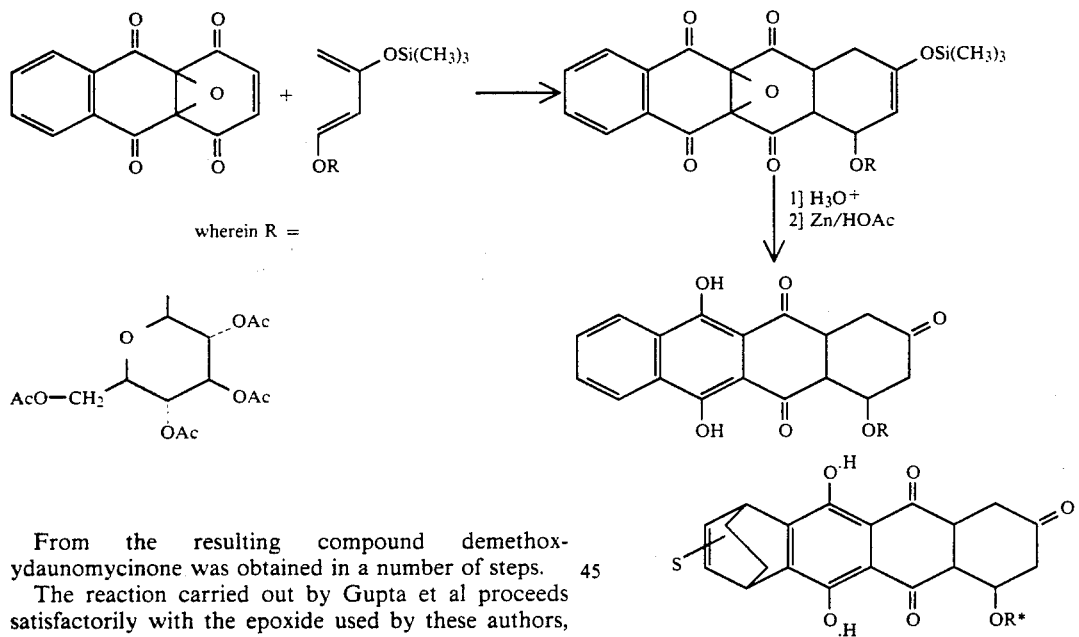

wherein R =

From the resulting compound demethoxydaunomycinone was obtained in a number of steps.

The reaction carried out by Gupta et al proceeds satisfactorily with the epoxide used by these authors, but with the naphtazarin used for the present synthesis, the reactivity appeared to be too low.

According to the invention 1-alkoxy-3-trimethylsilyloxy-1,3-butadienes of formula (1)

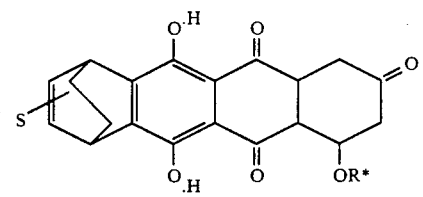

wherein R* is a group of the formula

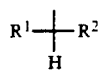

wherein R¹ is methyl and R² is an alkyl group containing at least 2 carbon atoms, or R¹ is an alkyl group having 1-4 carbon atoms and R² is an aryl group, a hetero aryl group, a —CH₂OR' group, a —CH₂N< group, a —CH₂—SR" group or a —CH₂—CH=CH₂ group, wherein R' and R" are alkyl groups having 1-4 carbon atoms; are used in the above reactions (a) and (b).

This results in a diastereomeric excess of the novel cyclic triketone compounds of formulae (2) and (3):

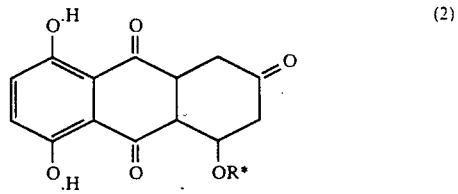

wherein S is H, alkyl or alkoxy and R* has the meaning given above.

The compounds of formula (1)

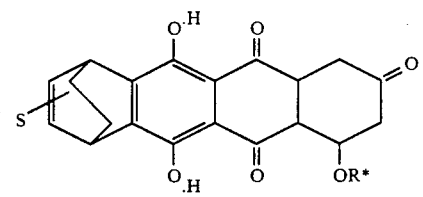

wherein R* has the meaning given above, are novel compounds.

The invention provides the above novel compounds both as individual stereoisomers and as mixtures thereof.

By analogy with the above synthesis of Kelly et al and Tolkiehn et al the following schemes can be employed, which schemes are only given by way of example.

scheme 1
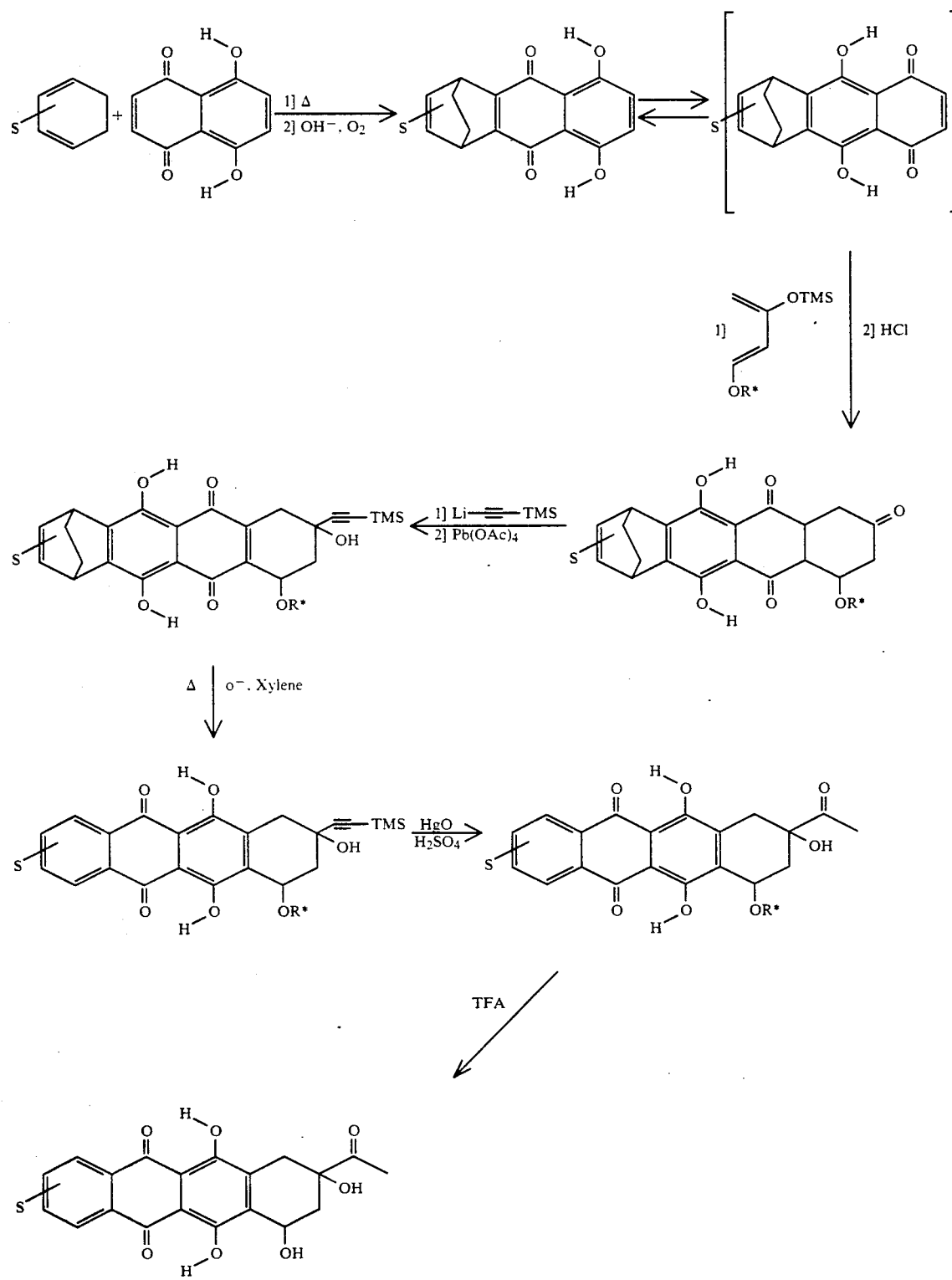
TMS = trimethylsilyl
TFA = trifluoro acetic acid scheme 2

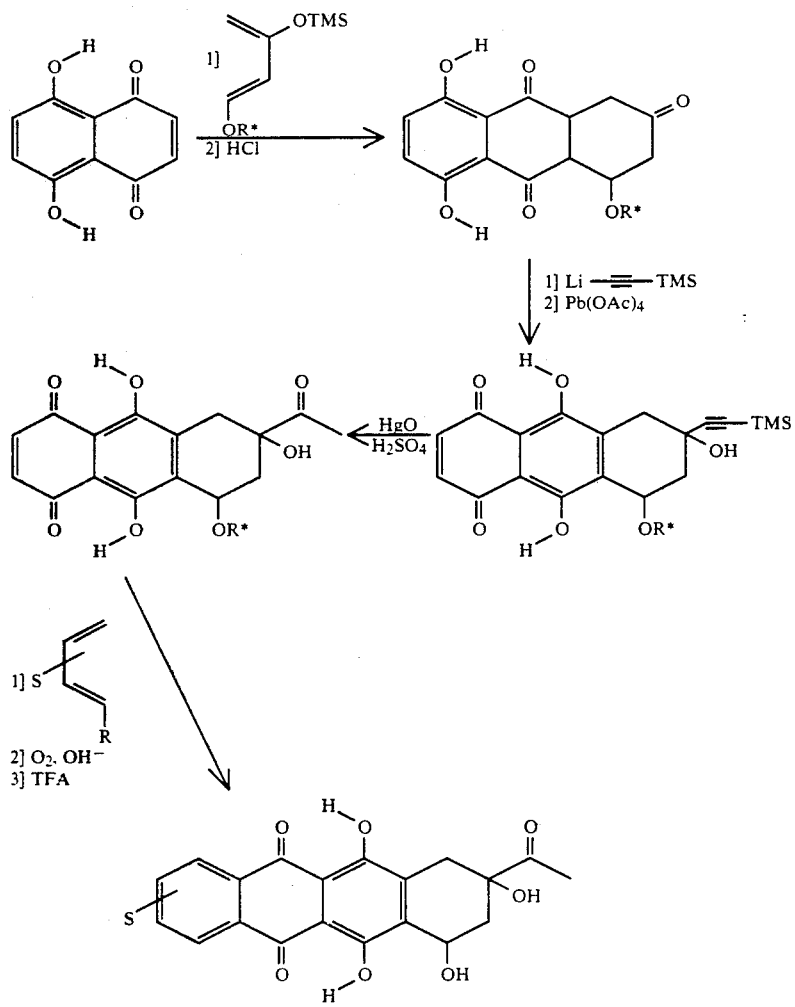

TMS = trimethylsilyl
TFA = trifluoro acetic acid

EXAMPLE 1

Reaction of chiral 1-alkoxy-3-trimethylsilyloxy-1,3-butadienes with naphtazarin and juglone General method

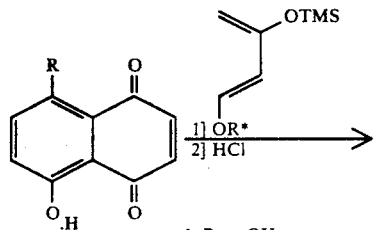

1: R = OH
2: R = H

-continued

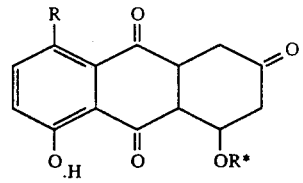

5.3 mmol of naphtazarin (sublimated) 1/juglone 2 was dissolved in 40 ml THF which had been distilled over sodium. During 5 minutes argon was passed over the solution and 1.5 equivalents (7.9 mmol) of diene was added. Thereafter argon was again passed over the solution for 5 minutes and the reaction mixture was stirred at room temperature for 16 hours. The reaction was monitored by means of TLC (ethyl acetate:n-hexane, 3:5).

After the reaction the reaction mixture was cooled to 0° C. and 1.5 ml of 1N HCl was added dropwise. The hydrolysis took 15 minutes and the reaction was followed by means of TLC (ethyl acetate:n-hexane, 3:5). The reaction was quenched by adding 15 ml of water and the product was extracted with CHCl$_3$ (3×50 ml). After drying the organic phase with Na$_2$SO$_4$ and evaporating, the crude product was dissolved in 5 ml of THF. This solution was slowly and dropwise added to 30 ml of n-hexane. The precipitate was filtered and washed with cold n-hexane (0° C.). The product was dried in a vacuum exsiccator over $P_2O_5$.

Yield for naphtazarin: 60-70%.
Yield for juglone: 70-80%.

EXAMPLE 2 a) Preparation of
1-(S(−)-1-phenylethyloxy-3-trimethylsilyloxy-1,3-butadiene and
1-(R(+)-1-phenylethyloxy(3-trimethylsilyloxy-1,3-butadiene (c)

This synthesis was carried out according to the following reaction scheme:

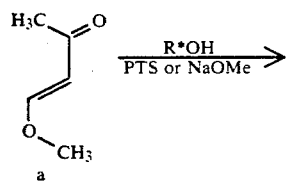

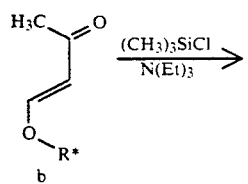

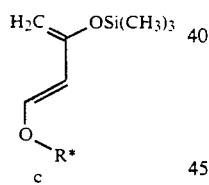

R* = 1-S-(−) or 1-R-(+)-phenylethyl group.
This method is described by S. Danishesky, M. Bernardski, T. Izawa and C. Maring, J.O.C. 49, 2290 (1984).

Starting from S(−)-1-phenylethanol ($[a_D^{20}] = -40.7°$, pure) or R(+)-1-phenylethanol ($[a_D^{20}] = 42.5°$, pure), the butenone (b) is prepared according to the above mentioned method of Danishefsky et al, to obtain 1-(S(−)-1-phenylethyloxy)-1-buten-3-one $[a_D^{20}] = -114.1°$, c=0.8 chloroform) and 1-(R(+)-1-phenylethyloxy)-1-buten-3-one ($[a_D^{20}] = +127.1°$, c=1.7 chloroform).

Thereafter, the optically active 1-alkoxy-3-trimethylsiliyloxy-1.3-butadiene (c) was synthesized according to the method of Danishefsky et al, starting from the optically active butenones (b). Result: S(−)c($[a_D^{20}] = -57.5°$, c=0.4 chloroform) and R(+)c($[a_D^{20}] = 59.3°$, c=0.6 chloroform).

b) Preparation of Diels-Alder product of naphtazarin with diene

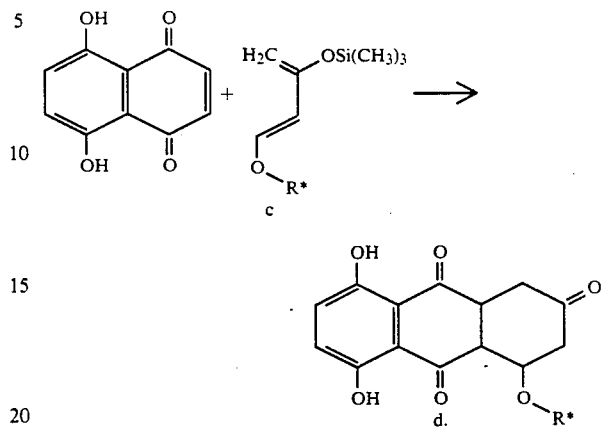

R* = 1-S-(−) or 1-R-(+)-phenylethyl group.
The Diels-Alder reactions of naphtazarin with the optically active dienes c were carried out as described in Example 1, to obtain S(−)d($[a_D^{20}] = +83.1°$, c=0.3 chloroform) and R(+)d($[a_D^{20}] = -83.6°$, c=0.2 chloroform).

c) Reaction of the Diels-Alder adduct with lithium trimethylsilyl acetylene and lead tetra acetate

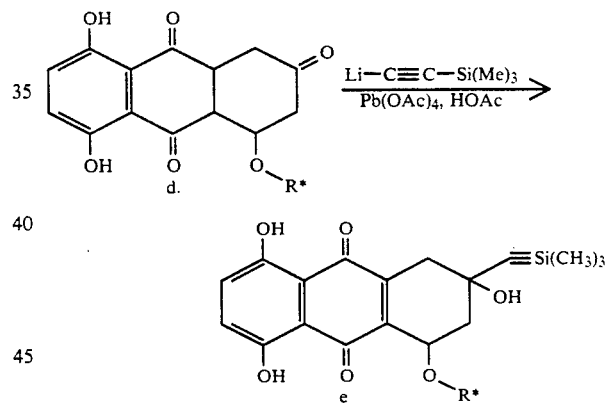

Trimethylsilyl acetylene (0.75 g, 7.6 mmol) is dissolved under an argon atmosphere in a mixture of 20 ml of THF (distilled over sodium) and 40 ml of toluene (distilled over sodium). The solution is cooled to −78° C., whereafter 1.6M n-butyllithium (4.35 ml, 6.95 mmol) is added. After stirring at −78° C. for half an hour ketone d (500 mg, 1.31 mmol), dissolved in a mixture of 5 ml of THF (distilled over sodium) and 10 ml of toluene (distilled over sodium), is added. The reaction mixture is stirred at −78° C. for 3 hours, while the course of the reaction is monitored by means of TLC (eluent-:ethyl acetate/n-hexane=2/5). Thereafter the reaction mixture is allowed to warm up to room temperature and then 25 ml of 10% ammonium chloride solution is added. After 15 minutes 50 ml of water is added and the mixture is twice extracted with 50 ml of chloroform. The collected organic fractions are dried with sodium sulphate, filtered and finally evaporated.

The resulting product is not first isolated but directly dissolved in 10 ml of glacial acetic acid, to which solution lead (IV) acetate (0.6 g, 4 mmI) is added to oxidize the product. After stirring for one night, 36 ml of water is added. The precipitated red solid is filtered off and rinsed from the filter with about 50 ml of chloroform. Finally, the solution is extracted with 15 ml of saturated sodium bicarbonate solution and the organic layer is dried with sodium sulphate, filtered and evaporated. The residue is purified by means of silicagel column chromatography (eluent:ethylacetate/n-hexane=1/4). Yield: 0.294 g (47%). The product is a mixture of 2 diastereomers S-S and S-R when the S-alcohol is used, and R-S and R-R when the R-alcohol is used. Optical rotations: $S(-)e[\alpha_D^{20}] = -26.5°$, c=0.1 dioxan; $-68.3$ (c=0.1 chloroform).

$R(+)e[_D^{20}] = 32.2°$, c=0.1, dioxan; +75.0° (c=0.1 chloroform), melting point 163°-167° C.

400 MHz $^1$H-NMR(CDCl$_3$) mixture of diastereomers $e_1$ and $e_2$, $\delta$=12.67 ppm(1H,s,ArOH diastereomer $e_1$), $\delta$=12.52 (1H,s,ArOH, diastereomer $e_1$), $\delta$=12.45 ppm (1H,s,ArOH, diastereomer $e_2$), $\delta$=12.43 ppm (1H,s,ArOH, diastereomer $e_2$), $\delta$=7.17-7.53 ppm (7H, m, ArH diastereomers $e_1$ and $e_2$), $\delta$=4.84-5.06 ppm (3H, OH, H(1), Ph-CH-Me, diastereomers $e_1$ and $e_2$), $\delta$=3.42-3.54 ppm (1H, H4(eq), diastereomers $e_1$ and $e_2$), $\delta$=2.70-2.85 ppm (1H, H4(ax), diastereomers $e_1$ and $e_2$), $\delta$=1.88-2.31 ppm (2H, H2(eq and ax), diastereomers $e_1$ and $e_2$), $\delta$=1.50 ppm(3H, d, CH$_3$, diastereomer $e_2$) $\delta$=1.42 ppm(3H,d,CH$_3$, diastereomer $e_1$), $\delta$=0.10 ppm (9H,s,(CH$_3$)$_3$, diastereomers $e_1$ and $e_2$).

The ratio of the two diastereomers can be determined from the $^1$H-NMR spectrum by intregration of the ArOH protons $\delta$=12.67+12.52:12.44 ppm and the CH$_3$ protons $\delta$=1.42:1.5 ppm. In the case of the S-(−)alcohol this ratio was 75:25.

The reaction leads to the cis-compound, i.e. wherein in ring A the —OH group at C-3 and the —OR group at C-3 have the cis-configuration with respect to each other. The difference between the cis-compound and trans-compound appears from the $^1$H-NMR spectrum wherein the coupling constant between H$_7$ and H$_8$ (ax) (R. P. Potman et al, J.O.C., 49, 3628 (1984) and literature cited therein) is less than that of the trans-compound. Furthermore, the shift difference between the geminal H$_1^0$ protons exceeds that of the trans-compound.

EXAMPLE 3

Summary of chiral inductions achieved with several butadienes and naphtazarin/juglon, vide example 1. Both a racemic mixture of the butadienes and the enantiomeric butadienes resulted in the same values for the diastereomeric excess; the values for the diastereomeric excess were determined from the NMR spectrum.

| | Chiral induction: | | |
|---|---|---|---|
| R* | diastereomeric excess of naphtazarin derivative | diastereomeric excess of juglone derivative | melting point naphtazarin derivative |
| (a) Me—⊢—Et, H | 5% | 3% | |
| (b) Me—⊢—i-Pr, H (O above) | 15% | 6% | |
| (c) Me—⊢—t-Bu, H (O above) | 30% | 15% | |
| (d) Ph—⊢—Me, H (O above) | 76% | 85% | 138°-140° C. |
| (e) Ph—⊢—Et, H (O above) | 50% | 57% | |
| (f) Ph—⊢—i-Pr, H (O above) | 27% | 49% | |
| (g) MeOCH$_2$—⊢—Me, H (O above) | 36% | 27% | |
| (h) p-MeO—Ph—⊢—Me, H (O above) | >90% | 65% | 162°-165° C. |
| (i) p-CF$_3$—Ph—⊢—Me, H (O above) | .57% | 46 | 114°-116° C. |
| (j) p-Cl—Ph—⊢—Me, H (O above) | 84% | 62 | 125°-128° C. |
| (k) p-CH$_3$—Ph—⊢—Me, H (O above) | 64% | 67 | 115°-118° C. |

$^1$H NMR data naphtazarin derivatives

In all cases mixtures of the diastereomers were obtained. For most products the chiral induction can be determined by integration of the two ArOH protons and the methyl protons of the chiral group. Furthermore, there are other protons which exhibit a shift difference for the diastereomers. However, in these cases it is often difficult to determine the ratio of the diastereomers by integration because of overlap of protons. For R*=Ph-CH-Me the complete $^1$H-NMR spectrum has been given, for the other compounds only the most characteristic protons such as ArOH and CH$_3$ have been given or only those protons which are of importance for the determination of the induction.

Compound (a)

$^1$H-NMR (90 MHz, CDCl$_3$, TMS internal standard): $\delta$=0.55 ppm(1.42H,d,J=6.3 Hz, CH$_3$), $\delta$=0.81 ppm(1.58H,d,J=6.3 Hz,CH$_3$), δ=11.80 ppm(1H,s,ArOH), δ=12.3 ppm(1H,s,ArOH).

Compound (b)

$^1$H-NMR(90 MHz,CDCl$_3$, TMS internal standard): δ=0.56 ppm(1.72H,d,J=6.3 Hz,CH$_3$), δ=0.77 ppm(1.28H,d,J=6.3 Hz,CH$_3$), δ=11.53 ppm(1H,s,ArOH), δ=12.01 ppm(1H,s,ArOH).

Compound (c)

$^1$H-NMR(400 MHz, CDCl$_3$, TMS internal standard): δ=0.35 ppm(3.15H,s, C(CH$_3$)$_3$), δ=0.48 ppm(5.85H,d,J=6.3 Hz,C(CH$_3$)$_3$), δ=0.51 ppm(1.05H, d,J=6.3 Hz,CH$_3$), δ=0.85 ppm(1.95H,d,J=6.3 Hz,CH$_3$), δ=11.51 ppm(0.65H,s, ArOH), δ=11.52 ppm (0.35H,s,ArOH), δ=12.01 ppm(0.35H,s, ArOH), δ=12.03 ppm(0.65H,s,ArOH).

Compound (d)

$^1$H-NMR (90 MHz,CDCl$_3$,TMS internal standard): δ=0.81 ppm(2.64H,d,J=6.3 Hz,CH$_3$), δ=1.08 ppm(0.36H,d,J=6.3 Hz,CH$_3$), δ=2.22-2.56 ppm(3H,m,H$_2$(ax) en H$_2$(eq)+H$_4$(ax), δ=3.35-3.75 ppm(3H,m,H$_4$(eq)+H$_5$+H$_6$), δ=3.96 ppm(1H, q,J=6.3 Hz,H$_1$CO), δ=4.23-4.43 ppm(1H,m,HCO), δ=6.56-6.71 ppm(0.24H,m, ArH), δ=6.92-7.06 ppm(1.76H,m,ArH), δ=7.13-7.29 ppm(5H,m,ArH), δ=11.58 ppm(1H,s,ArOH), δ=11.88 ppm(0.12H,s,ArOH), δ=12.11 ppm(0.88H,s,ArOH).

Compound (e)

$^1$H-NMR (90 MHz,CDCl$_3$,TMS internal standard): δ=0.24 ppm(2.25H,t,J=7.5 Hz,CH$_3$), δ=0.60 ppm(0.75H,t,J=7.5 Hz,CH$_3$), δ=11.60 ppm(1H,s,ArOH), δ=11.86 ppm(0.25H,s,ArOH), δ=12.08 ppm(0.75H,s,ArOH).

Compound (f)

$^1$H-NMR (90 MHz,CDCl$_3$,TMS internal standard); δ=0.34 ppm(1.90H,d,J=6.3 Hz,CH$_3$), δ=0.79 ppm(1.10H,d,J=6.3 Hz,CH$_3$), δ=11.58 ppm(0.63H,s, ArOH), δ=11.89 ppm(0.37H,s,ArOH), δ=12.08 ppm(1H,s,ArOH).

Compound (g)

$^1$H-NMR(90 MHz,CDCl$_3$,TMS internal standard): δ=0.56 ppm(2.04H,d,J=6.3 Hz,CH$_3$), δ=0.79 ppm(0.96H,d,J=6.9 Hz,CH$_3$), δ=11.56 ppm(1H,s,ArOH), δ=12.03 ppm(0.68H,s,ArOH), δ=12.06 ppm(0.32H,s,ArOH).

Compound (h)

$^1$H-NMR(90 MHz,CDCl$_3$,TMS internal standard): δ=0.76 ppm(2.88H,d,J=6.3 Hz, CH$_3$), δ=1.03 ppm(0.12H,d,J=6.3 Hz,CH$_3$), δ=11.58 ppm(1H,s,ArOH), δ=11.86 ppm(0.04H,s,ArOH), δ=12.11 ppm(0.96H,s,ArOH).

Compound (i)

$^1$H-NMR(90 MHz,CDCl$_3$,TMS internal standard): δ=0.82 ppm(2.36H,d,J=6.3 Hz,CH$_3$), δ=1.11 ppm(0.64H,d,J=6.3 Hz,CH$_3$), δ=11.51 ppm(1H,s,ArOH), δ=11.86 ppm(0.22H,s,ArOH), δ=12.08 ppm(0.78H,s,ArOH).

Compound (j)

$^1$H-NMR(90 MHz,CDCl$_3$,TMS internal standard): δ=0.75 ppm(2.76H,d,J,6.3 Hz,CH$_3$), δ=1.04 ppm(0.24H,d,J=6.3 Hz,CH$_3$), δ=11.49 ppm(1H,s,ArOH), δ=11.81(0.08H,s,ArOH), δ=12.03 ppm(0.92H,s,ArOH).

Compound (k)

$^1$H-NMR(90 MHz,CDCl$_3$,TMS internal standard): δ=0.74 ppm(2.46H,d,J=6.3 Hz, CH$_3$), δ=1.04 ppm(0.54H,d,J=6.3 Hz,CH$_3$), δ=11.60 ppm(1H,s,ArOH), δ=11.89 ppm(0.18H,s,ArOH), δ=12.12 ppm(0.82H,s,ArOH).

EXAMPLE 4

A number of new 1-alkoxy-3-trimethylsilyloxy-1,3-butadienes (1)

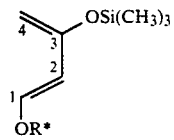

were prepared according to the above mentioned method of Danishefsky et al

| | R* = | Total yield[a] | Boiling point |
|---|---|---|---|
| 1 | Me—CH—Et | 71% | 59-60° C. (1 mm Hg) |
| 2 | Me—CH-i-Pr | 69% | 65-67° C. (1.5 mm Hg) |
| 3 | Me—CH-t-Bu | 67% | 80-82° C. (1 mm Hg) |
| 4 | Ph—CH—Me | 68% | 115-120° C. (0.1 mm Hg) |
| 5 | Ph—CH—Et | 64% | 119-121° C. (0.1 mm Hg) |
| 6 | Ph—CH-i-Pr | 54% | 110-115° C. (0.1 mm Hg) |
| 7 | MeO—CH$_2$—CH—Me | 88% | 81° C. (1 mm Hg) |
| 8 | p-MeO—Ph—CH—Me | 60% | 145° C. (0.35 mm Hg) |
| 9 | p-Me—Ph—CH—Me | 61% | 124-126° C. (0.5 mm Hg) |
| 10 | p-Cl—Ph—CH—Me | 13% | 127° C. (0.5 mm Hg) |
| 11 | p-CF$_3$—Ph—CH—Me | 63% | 123-124° C. (0.5 mm Hg) |

[a] Yield calculated with respect to alcohol and 1-methoxy-1-buten-3-one.

NMR data: $^1$H-NMR, 90 MHz, CDCl$_3$, TMS as internal standard.

1: δ=6.6 ppm (1H,d,J=12 Hz,H(1)), δ=5.4 ppm (1H,d,J=12 Hz,H(2)), δ=3.9 ppm(2H,s,H(4)), δ=2.5 ppm(1H,m,CH), δ=1.1 ppm(3H,d,CH$_3$), δ=0.9 ppm(2H,m,CH$_2$), δ=0.8 ppm(3H,t,CH$_3$), δ=0.2 ppm(9H,s,OSi(CH$_3$)$_3$).

2: δ=6.5 ppm(1H,d,J=12 Hz,H(1)), δ=5.3 ppm(1H,d,J=12 Jz,H(2)), δ=3.9 ppm (2H,s,H(4)), δ=2.1 ppm(1H,m,CH), δ=1.6 ppm(1H,m,CH), δ=1.1 ppm(3H,d,CH$_3$), δ=0.9 ppm(6H,d,CH$_3$), δ=0.2 ppm(9H,s, OSi(CH$_3$)$_3$).

3: δ=6.5 ppm(1H,d,J=12 Hz,H(1)), δ=5.3 ppm(1H,d,J=12 Hz,H(2)), δ=4.0 ppm(2H,s,H(4)), δ=2.2 ppm(1H,m,CH), δ=1.1 ppm(3H,d,CH$_3$), δ=0.7 ppm(9H,s,(CH$_3$)$_3$), δ=0.2 ppm(9H,s,OSi(CH$_3$)$_3$).

4: δ=7.17 ppm(5H,br,s,ArH), δ=6.53 ppm(1H,d,J=12 Hz,H(1)), δ=5.4 ppm(1H,d,J=12 Hz,H(2)), δ=4.77 ppm(1H,q,OCH), δ=3.96 ppm(2H,s,H(4)), δ=1.5 ppm(3H,d,CH$_3$), δ=0.2 ppm(9H,s,OSi(CH$_3$)$_3$).

5: δ=7.0 ppm(5H,br s,ArH), δ=6.4 ppm(1H,d,J=12 Hz,H(1)), δ=5.2 ppm (1H,d,J=12 Hz,H(2)), δ=4.5 ppm(1H,t,OCH), δ=3.8 ppm(2H,s,H(4)), δ=1.8 ppm(2H,m,CH$_2$), δ=0.8 ppm(3H,t,CH$_3$), δ=0.2 ppm(9H,s,OSi(CH$_3$)$_3$).

6: δ=7.2 ppm(5H,br, s,ArH), δ=6.6 ppm(1H,d,J=12 Hz,H(1)), δ=5.4 ppm(1H,d,J=12 Hz,H(2)), δ=4.4 ppm(1H,d,OCH), δ=4.0 ppm(2H,s,H(4)), δ=1.9 ppm(1H,m,CH), δ=1.0 ppm(6H,d,CH$_3$), δ=0.2 ppm(9H,s,OSi(CH$_3$)$_3$).

7: δ=6.6 ppm(1H,d,J=12 Hz,H(1)), δ=5.3 ppm(1H,d,J=12 Hz,H(2)), δ=4.0 ppm(2H,br s,H(4)), δ=3.3 ppm(2H,d,CH2), δ=3.3 ppm (3H,s, OCH3), δ=2.2 ppm(1H,m,CH), δ=1.1 ppm(3H,d,CH3), δ=0.2 ppm(9H,s,OSi(CH3)3).

8: δ=7.23 ppm(2H,d,ArH), δ=6.82 ppm (2H,d,ArH), δ=6.67 ppm(1H,d,J=12 Hz, H(1)), δ=5.43 ppm(1H,d,J=12 Hz,H(2)), δ=4.82 ppm(1H,q,OCH), δ=4.03 ppm(2H,s,H(4)), δ=3.75 ppm(3H,s,OCH3), δ=1.5 ppm(3H,d,CH3), δ=0.17 ppm(9H,s,OSi(CH3)3).

9: δ=7.13 ppm(4H,s,ArH), δ=6.61 ppm(1H,d,J=12 Hz,H(1)), δ=5.39 ppm(1H,d,J=12 Hz,H(2)), δ=4.80 ppm(1H,q,J=6.3 Hz,HCO), δ=4.00 ppm(2H,s,H(4)), δ=2.32 ppm(3H,s,p-Me),=1.53 ppm(3H,d,J=6.3 Hz, CH3), δ=0.17 ppm (9H,s,OSi(CH3)3).

10: δ=7.27 ppm(4H,m,ArH), δ=6.60 ppm(1H,d,J=12 Hz,H(1)), δ=5.42 ppm (1H.d,J=12 Hz,H(2), δ=4.83 ppm(1H,q,J=6.3 Hz,HCO), δ=4.05 ppm(2H,s,H(4)), δ=1.53 ppm(3H,d,J=6.3 Hz,CH3), δ=0.17 ppm (9H,s,OSi(CH3)3).

11: δ=7.53 ppm(4H,m,ArH), δ=6.67 ppm(1H,d,J=12 Hz,H(1)), δ=5.46 ppm(1H,d,J=12 Hz, H(2)), δ=4.82 ppm(1H,q,J=6.3 Hz,HCO), δ=3.93 ppm(2H,s,H(4)), δ=1.39 ppm(3H,d,J=6.3 Hz,CH3), δ=0.17 ppm(9H,s,OSi(CH3)3).

We claim:

1. 1-alkoxy-3-trimethylsilyloxy-1,3-butadienes of formula (1)

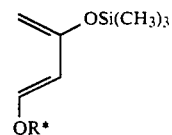 (1)

wherein R* is a group of the formula

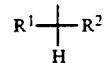

wherein $R^1$ is methyl and $R^2$ is an alkyl group containing at least 2 carbon atoms, or $R^1$ is an alkyl group having 1-4 carbon atoms and $R^2$ is selected from the group consisting of an aryl group, a —CH2OR' group, a —CH2N< group, a —CH2SR" group and a —CH2—CH=CH2 group, and wherein R' and R" are alkyl groups having 1-4 carbon atoms.

2. A butadiene (1) according to claim 1, wherein $R^1$ is methyl and $R^2$ is p-methoxyphenyl.

3. A butadiene (1) according to claim 1, wherein $R^1$ is methyl and $R^2$ is phenyl.

4. A butadiene (1) according to claim 1, wherein $R^1$ is ethyl and $R^2$ is phenyl.

5. A butadiene (1) according to claim 1, wherein $R^1$ is methyl and $R^2$ is p-trifluoromethylphenyl.

6. A butadiene (1) according to claim 1, wherein $R^1$ is methyl and $R^2$ is p-chlorophenyl.

7. A butadiene (1) according to claim 1, wherein $R^1$ is methyl and $R^2$ is p-methylphenyl.

8. A butadiene (1) according to claim 1, wherein $R^2$ is an aryl group.

9. A butadiene (1) according to claim 8, wherein $R^2$ is a phenyl group.

10. A butadiene (1) according to claim 9, wherein said phenyl group is unsubstituted.

* * * * *